United States Patent [19]

Aoki et al.

[11] Patent Number: 5,248,803
[45] Date of Patent: Sep. 28, 1993

[54] SILANE COMPOUND AND PROCESSES FOR THE PREPARATION THEREOF

[75] Inventors: Tomoko Aoki; Kunihiko Imanishi; Ryuji Sato, all of Iruma; Satoshi Ueki, Shiki; Yoshiharu Okumura, Tokyo; Tadanao Kohara, Urawa, all of Japan

[73] Assignee: Tonen Corporation, Tokyo, Japan

[21] Appl. No.: 960,585

[22] Filed: Oct. 13, 1992

[30] Foreign Application Priority Data

Oct. 16, 1991 [JP] Japan .................. 3-294910
Oct. 30, 1991 [JP] Japan .................. 3-310015
Feb. 28, 1992 [JP] Japan .................. 4-75898
Mar. 9, 1992 [JP] Japan .................. 4-84968

[51] Int. Cl.$^5$ ............................ C07F 7/18
[52] U.S. Cl. .................................. 556/482
[58] Field of Search ........................ 556/482

[56] References Cited

PUBLICATIONS

Noll, "Chemistry and Technology of Silanes", Academic Press, N.Y. (1968), pp. 81 and 82.

*Primary Examiner*—Paul F. Shaver
*Attorney, Agent, or Firm*—Kane, Dalsimer, Sullivan, Kurucz, Levy, Eisele and Richard

[57] ABSTRACT

Novel silane compound, alkoxy cyclopentyl dimethoxysilane, is prepared by reacting cyclopentyl trihalosilane with ROH and then with methanol, or by reacting cyclopentyl trimethoxysilane with ROH, wherein alkyl in the alkoxy or R in ROH stands for an organic group selected from the group consisting of sec-butyl, tert-amyl, cyclopentyl, oxa-3-cyclopentyl, cyclohexyl and 2-isopropyl-5-methyl cyclohexyl groups. The silane compounds are useful as a catalytic component for olefin polymerization and as a silane coupling agent.

1 Claim, 12 Drawing Sheets

SILANE COMPOUND AND PROCESSES FOR THE PREPARATION THEREOF

FIELD OF THE INVENTION

This invention relates to a novel silane compound and processes for the preparation thereof, more specifically a novel silane compound which is suitable as a catalytic component for polymerization of olefin, particularly propylene, or as a silane coupling agent, and processes for the preparation thereof.

PRIOR ART

It is known that a polymer with high stereoregularity can be prepared by the use of alkoxy silanes as a catalytic component in the polymerization of propylene. However, it was impossible to sufficiently attain both high polymerization activity and high stereoregularity with known alkoxy silanes as a catalytic component in the polymerization of propylene.

Further, silane compounds are expected to be useful as silane coupling agents and resin modifiers. Accordingly, new silane compounds are awaited.

SUMMARY OF THE INVENTION

One object of the invention is to provide a novel silane compound.

Another object of the invention is to provide processes for the preparation of the novel silane compound.

The present invention provides a silane compound represented by the following formula (I):

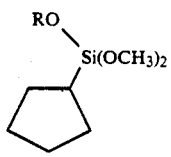

(I)

wherein R represents an organic group selected from the group consisting of sec-butyl, tert-amyl, cyclopentyl, oxa-3-cyclopentyl, cyclohexyl and 2-isopropyl-5-methyl cyclohexyl groups. Thus, the novel silane compound is sec-butoxy cyclopentyl dimethoxysilane (I-1), tert-amyloxy cyclopentyl dimethoxysilane (I-2), cyclopentyloxy cyclopentyl dimethoxysilane (I-3), cyclopentyl dimethoxy oxa-3-cyclopentyloxysilane (I-4), cyclohexyloxy cyclopentyl dimethoxysilane (I-5), and cyclopentyl (2-isopropyl-5-methyl cyclohexyloxy) dimethoxysilane (I-6).

The invention also provides a process for the preparation of the silane compound represented by the above formula (I), characterized in that cyclopentyl trihalosilane is reacted with ROH, wherein R has the same meaning as above, and then a resultant reaction product is reacted with methanol.

The invention further provides another process for the preparation of the silane compound represented by the above formula (I), characterized in that cyclopentyl trimethoxysilane is reacted with ROH via exchange of alkoxy groups, wherein R has the same meaning as above.

DETAILED DESCRIPTION OF THE INVENTION

Figure 1:
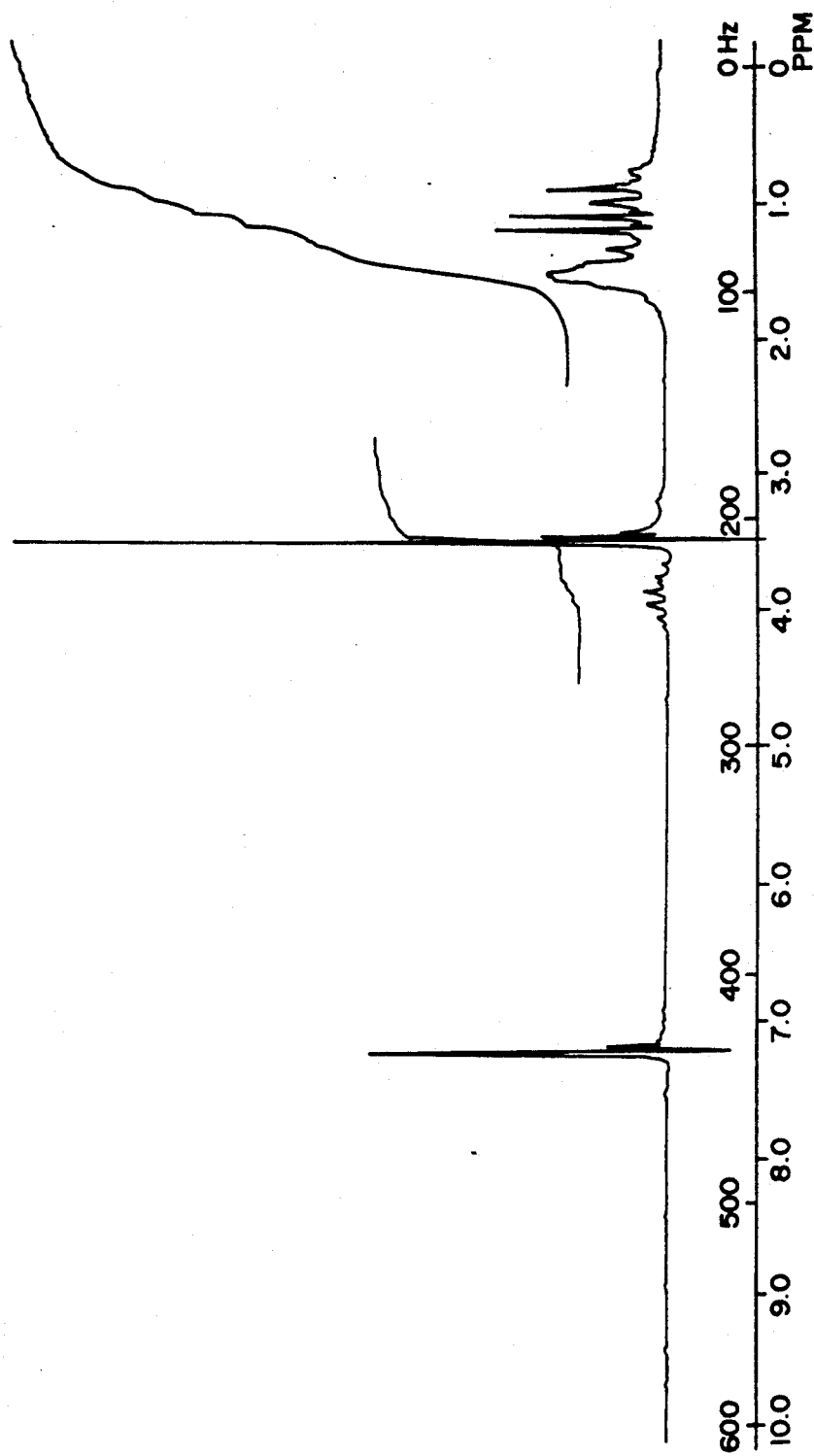
FIGS. 1 and 2 are charts of $^1$H-NMR and IR, respectively, on compound (I-1) obtained in Example 2.

Oxa-3-cyclopentyl group in compound (I-4) has the following structure:

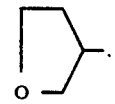

2-Isopropyl-5-methyl cyclohexyl group (or p-menthane-3-yl for short) in compound (I-6) has the following structure:

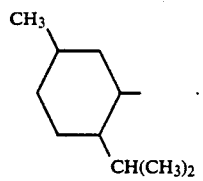

These silane compounds (I-1) to (I-6) have the following boiling points:

| | |
|---|---|
| (I-1) | 99° C./16 mmHg, |
| (I-2) | 95° C./1.9 mmHg, |
| (I-3) | 125° C./6 mmHg, |
| (I-4) | 77° C./10 mmHg, |
| (I-5) | 95° C./0.1 mmHg, and |
| (I-6) | 101° C./0.1 mmHg. |

The structures of these silane compounds may be confirmed by GC-MS, $^1$H-NMR, infrared absorption spectrum (IR) and so on.

When silane compounds (I-1) to (I-6) are analyzed by $^1$H-NMR, signals are observed at δ0.7 to 1.9 for —CH$_3$ and —C$_2$H$_5$ of the sec-butyl group and the cyclopentyl group, δ3.50 for the methoxy groups, and δ3.93 for

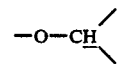

of the butoxy group in the case of compound (I-1);

δ0.7 to 1.5 for the tert-amyloxy groups, δ1.5 to 2.2 for the cyclopentyl group, and δ3.52 for the methoxy groups in the case of compound (I-2);

δ1.1 to 1.9 for the cyclopentyl group and the hydrogen atoms except one bound to the carbon atom directly bound to the oxygen atom in the cyclopentyloxy group, δ3.47 for the methoxy groups and δ4.40 for the hydrogen atom bound to the carbon atom directly bound to the oxygen atom in the cyclopentyloxy group in the case of compound (I-3);

δ0.8 to 2.2 for the cyclopentyl group and the hydrogen atoms of the methylene group at position 4 of the oxa-3-cyclopentyl group, δ3.52 for the methoxy groups, δ4.60 for the hydrogen atom bound to the carbon atom at position 3 of the oxa-3-cyclopentyl group, and δ3.4 to 4.0 for the other hydrogen atoms of the oxa-3-cyclopentyl group in the case of compound (I-4);

δ0.6 to 2.0 for —CH₂— in the cyclohexyl group, and the cyclopentyl group, δ3.45 for the methoxy groups, δ3.8 for

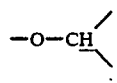

of the cyclohexyloxy group in the case of compound (I-5); and

δ0.6 to 1.2 for the hydrogen atoms bound to the carbon atoms at the positions other than position 1, δ1.4 to 2.0 for the cyclopentyl group, δ3.55 for the methoxy group and δ3.75 for

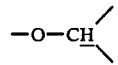

of the 2-iso-propyl-5-methyl cyclohexyl group in the case of compound (I-6).

In analysis by IR spectra, a large absorption due to the SiOC bonds is observed around 1,100 cm⁻¹ in every compound.

Olefinic polymers, such as polypropylene and polybutene, with high stereoregularity can be prepared at high polymerization activity using the silane compound (I) as a catalytic component.

As the silane compound (I) has hydrolytic groups, it can be used as a silane coupling agent, a polymerizable monomer and a resin modifier.

The invention also provides a process for the preparation of the novel silane compound represented by the aforesaid formula (I), wherein cyclopentyl trihalosilane is reacted with ROH, wherein R has the same meaning as defined above, and a resultant reaction product is reacted with methanol. The starting material, cyclopentyl trihalosilane is represented by the following formula (II):

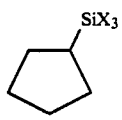

where X stands for a halogen atom, preferably Cl or Br. It may easily be prepared from cyclopentene and trihalosilane, i.e., H-SiX₃ through hydrosilylation reaction:

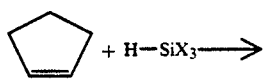

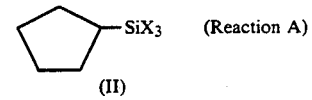

In the above reaction, 0.9 to 1.1 moles of trihalosilane may be used per mole of cyclopentene. The reaction is conducted in conditions of a temperature of 100° to 200° C. and 10 minutes to 10 hours, preferably with the use of a platinum catalyst such as chloroplatinic acid and platinum-1,1,3,3-tetramethyl-1,3-divinyldisiloxane complex. Solvents may also be used, such as benzene and toluene.

In the invention, the cyclopentyl trihalosilane (II) is reacted with ROH, wherein R has the same meaning as defined above, as follows:

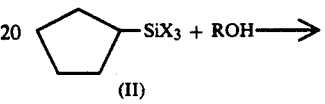

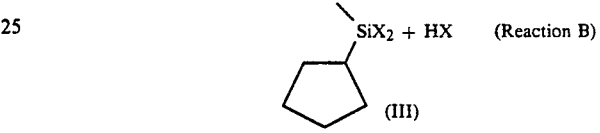

In the above reaction, 1 to 3 moles of ROH may be used per mole of cyclopentyl trihalosilane (II). The reaction may be carried out at a temperature of, for instance, 20° to 100° C. for 10 minutes to 5 hours, preferably at a temperature of 40° to 70° C. for 30 minutes to 2 hours. Solvents may be used, such as organic solvents, for instance, hexane, ethers, petroleum ether and benzene.

In the invention, it is preferred to use a hydrogen halide acceptor in the reaction mixture in order to facilitate the reaction. Examples of the hydrogen halide acceptor include tertiary amines, and nitrogen-containing heterocyclic compounds such as pyridine, quinoline and isoquinoline with pyridine and quinoline being preferred. 1 to 1.5 moles of the hydrogen halide acceptor are preferably used per mole of cyclopentyl trihalosilane.

The resultant reaction product (III) is then reacted with methanol according to the invention to prepare the silane compound (I) of the invention as follows:

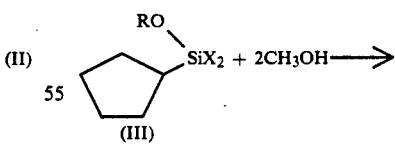

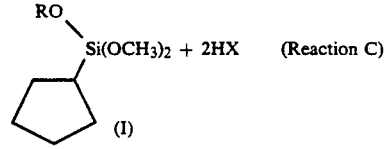

In the above reaction, 2 to 3 moles of methanol may be used per mole of the compound (III). The reaction may be carried out at a temperature of 0° to 100° C. for 10 minutes to 5 hours, preferably a temperature of 10° to 60° C. for 30 minutes to 2 hours. It is preferred to use a hydrogen halide acceptor also in Reaction C in order to facilitate the reaction. The hydrogen halide acceptors mentioned for Rection B may be used also here. A hydrogen halide acceptors used here may be the same as or different from one used in Reaction B, but is generally the same as that. 2 to 3 moles of a halogen halide acceptor are preferably used per mole of the compound (III).

In the above reactions B and C, an inert gas may be blown in the remove formed hydrogen halide from the reaction system so as to facilitate the reactions.

The novel silane compound (I) may be prepared at high yield in the aforesaid process.

The invention also provide another process for the preparation of the silane compound represented by the formula (I), wherein cyclopentyl trimethoxysilane is reacted with ROH via exchange of alkoxy groups, wherein R has the same meaning as defined above.

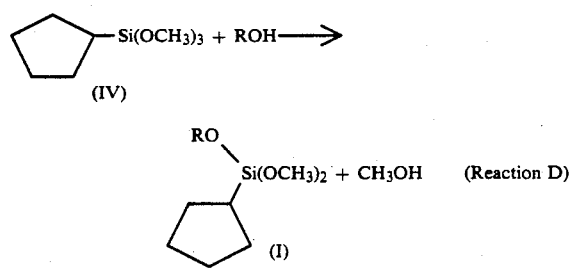

1 to 20 moles of ROH may be used per mole of the compound (IV). The reaction may be carried out at a temperature of 0° to 100° C. (or 0° to 150° C. for compound I-2), for 10 minutes to 20 hours. In this alkoxy groups exchange reaction, catalyst may be used such as acids, for instance, trifluoroborane-ether complexes and toluene sulfonic acid, or ones which react with alcohol to form acid, such as trimethyl chlorosilane; or bases, for instance, alkali metal alkoxides and metal hydroxides.

The starting material, cyclopentyl trimethoxysilane (IV), may be prepared by reaction of cyclopentyl trichlorosilane with methanol to form hydrogen halide.

The invention will further be explained with reference to the following Examples, but the invention shall not be limited by the Examples.

EXAMPLES

The $^1$H-NMR and IR measurements were conducted in the following conditions.
$^1$H-NMR
Unit
Solvent: CCl$_4$
Standard reference material: CHCl$_3$ and tetramethylsilane (TMS)
IR
Unit: 1600 Series FT-IR (Perkin Elmer)
Method: liquid film method (KBr plate).
For GC-MS measurement, HP 5970 B (Hewlett-Packard) was used.

EXAMPLE 1

Preparation of sec-Butoxy Cyclopentyl Dimethoxysilane (I-1)

In a 100 ml autoclave were charged 16.7 g (0.245 mole) of cyclopentene, 30.1 g (0.222 mole) of trichlorosilane and 25 μl of a 0.077 m mole/ml chloroplatinic acid solution in isopropyl alcohol (platinum content 1.92×10$^{-6}$ mole), which were then stirred at 150° C. for 30 minutes. Cyclopentyl trichlorosilane was obtained quantitatively.

In a 500 ml three-neck flask provided with a magnetic stirrer, a reflux condenser and a dropping funnel were charged 36.6 g (0.180 mole) of the cyclopentyl trichlorosilane prepared above and 300 ml of hexane, to which a mixture of 45.6 g (0.576 mole) of pyridine and 17.3 g (0.234 mole) of sec-butyl alcohol was added dropwise over a period of 30 minutes at room temperature under stirring. After stirring for further 30 minutes, 16.7 g (0.522 mole) of methanol were added and stirring was continued for further 30 minutes and then the reaction was ended.

After a salt formed was filtered off and hexane was distilled off, a liquid of 28.6 g (0.123 mole) with a boiling point of 99° C./16 mmHg was obtained by vacuum distillation. This product was confirmed to be sec-butoxy cyclopentyl dimethoxysilane by GC-MS, $^1$H-NMR and IR. The yield was 68%.

The GC-MS measurement results, m/e vs. spectral intensity ratios in parentheses, are as follows: 203(16), 163(27), 135(43), 107(100), 91(29), 77(37), 59(23).

EXAMPLE 2

Another Preparation of sec-Butoxy Cyclopentyl Dimethoxysilane (I-1)

Figure 2:
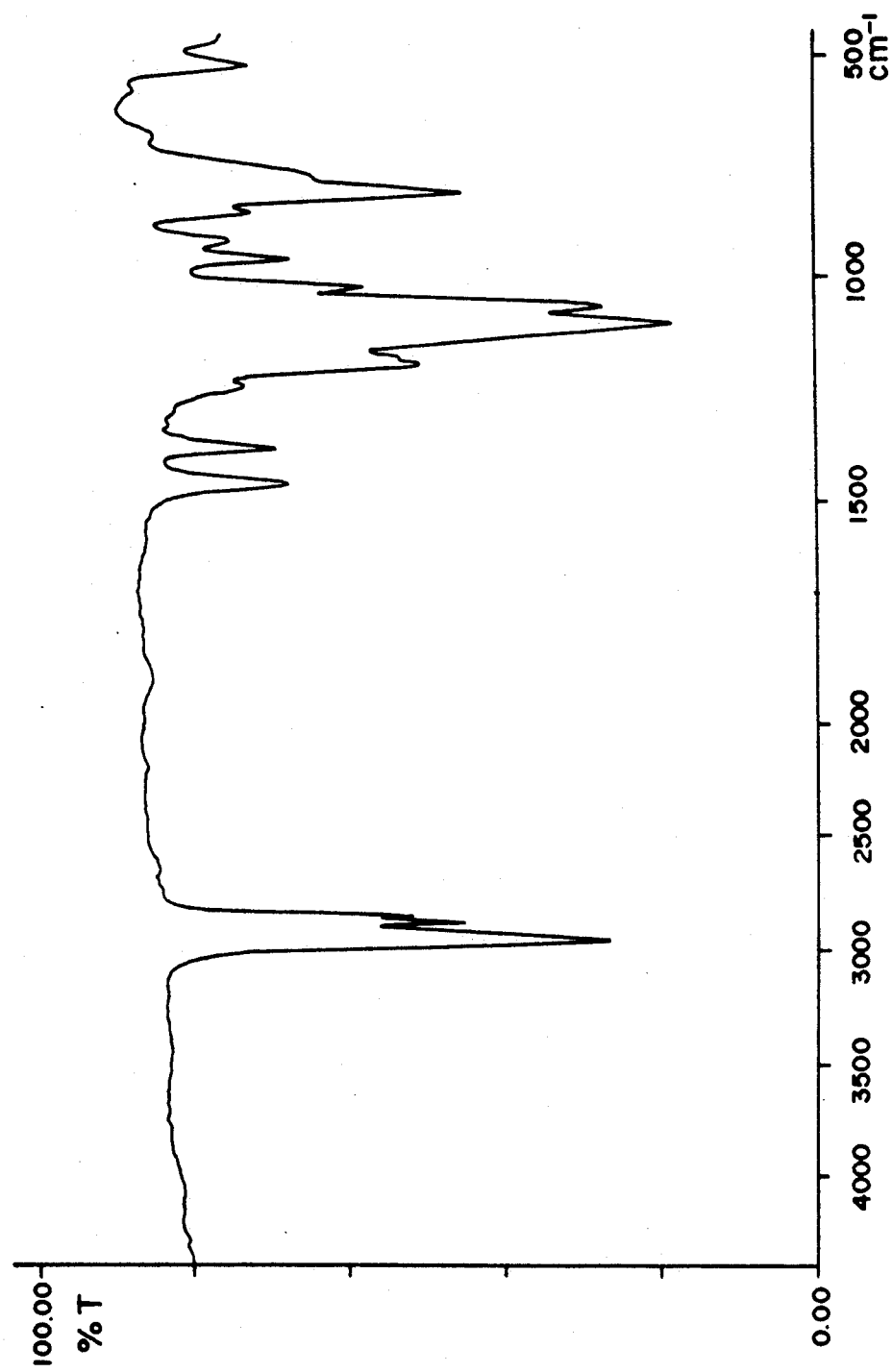

In a 100 ml three-neck flask provided with a magnetic stirrer were charged 10.3 g (0.0542 mole) of cyclopentyl trimethoxysilane, 40.3 g (0.543 mole) of sec-butyl alcohol and 33.7 mg (0.625 m mole) of sodium methoxide, which were then reacted with each other at room temperature for 2 hours under stirring. Then, trimethylchlorosilane was added to neutralize the alkali. Then, 10.6 g (0.0457 mole) of sec-butoxy cyclopentyl dimethoxysilane were obtained by vacuum distillation. Its structure was confirmed as in Example 1. FIGS. 1 and 2 are charts of $^1$H-NMR and IR, respectively. The yield was 84%.

EXAMPLE 3

Preparation of Cyclohexyloxy Cyclopentyl Dimethoxysilane (I-5)

The procedures of Example 1 were repeated with the exception that 39.7 g (0.195 mole) of cyclopentyl trichlorosilane, 51.0 g (0.644 mole) of pyridine, 18.1 g (0.566 mole) of methyl alcohol, and 23.0 g (0.230 mole) of cyclohexanol in place of sec-butyl alcohol were used. 35.8 g (0.138 mole) of the product with a boiling point of 95° C./0.1 mmHg were obtained.

The product was confirmed to be cyclohexyloxy cyclopentyl dimethoxysilane by GC-MS, $^1$H-NMR and IR. The yield was 71%.

The GC-MS results, m/e vs. spectral intensity in parentheses, are as follows: 189(56), 147(10), 131(10), 107(100), 91(19), 77(25).

EXAMPLE 4

Another Preparation of Cyclohexyloxy Cyclopentyl Dimethoxysilane (I-5)

Figure 3:
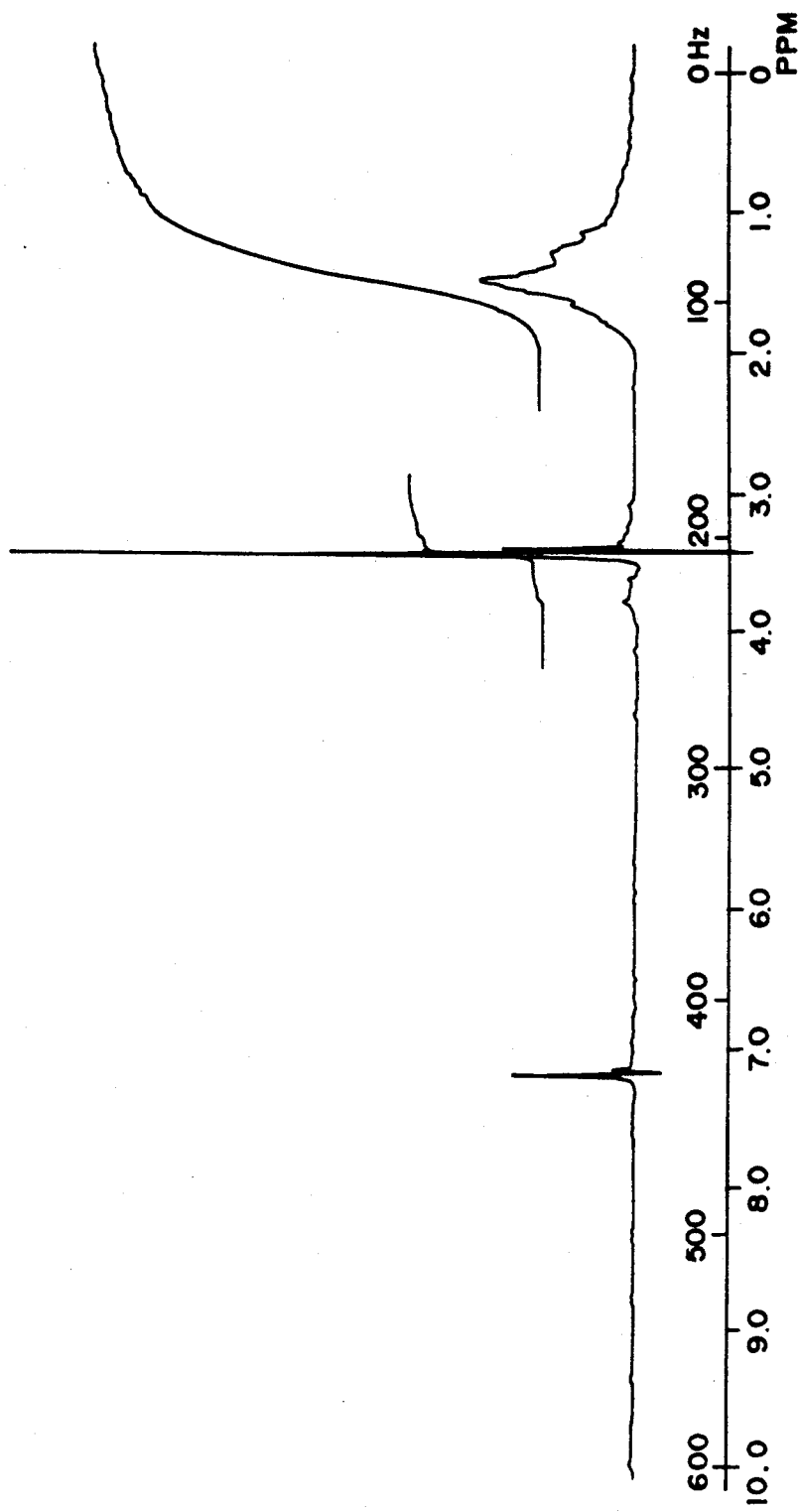
FIGS. 3 and 4 are charts of $^1$H-NMR and IR, respectively, on compound (I-5) obtained in Example 4.
Figure 4:
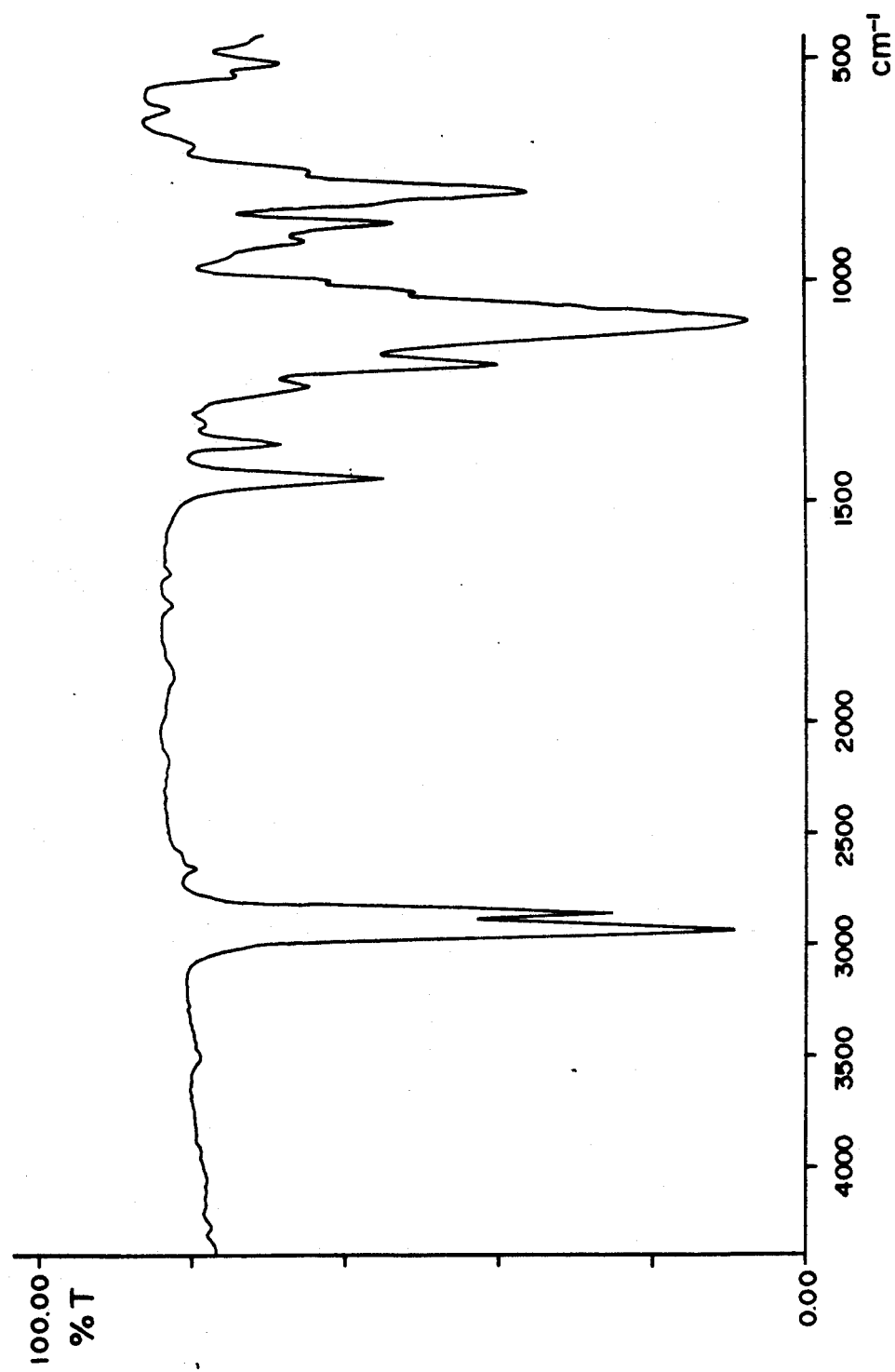

The procedures of Example 2 were repeated with the exception that 10.0 g (0.0526 mole) of cyclopentyl trimethoxysilane, 85.1 mg (1.58 m mole) of sodium methoxide, and 52.7 g (0.526 mole) of cyclohexanol in place of sec-butyl alcohol were used and the reaction time was one and a half hours. Then, 11.3 g (0.0438 mole) of cyclohexyloxy cyclopentyl dimethoxysilane were obtained. Its structure was confirmed as in Example 1. FIGS. 3 and 4 are the charts of $^1$H-NMR and IR, respectively. The yield was 83%.

EXAMPLE 5

Preparation of Cyclopentyl (2-Isopropyl-5-Methyl Cyclohexyloxy) Dimethoxysilane (I-6)

The procedures of Example 1 were repeated with the exception that 200 ml of hexane, 45.4 g (0.574 mole) of pyridine, 17.9 g (0.559 mole) of methyl alcohol, and a solution of 39.4 g (0.252 mol) of (−)-menthol, in place of sec-butyl alcohol, in 100 ml hexane were used to obtain 39.6 g (0.126 mole) of cyclopentyl (2-isopropyl-5-methyl cyclohexyloxy) dimethoxysilane. Its structure was confirmed as in Example 1. The yield was 70%. The GC-MS results, m/e vs. spectral intensity in parentheses, are as follows: 245(25), 229(93), 161(51), 138(61), 137(52), 131(36), 107(100), 91(58), 81(89).

EXAMPLE 6

Another Preparation of Cyclopentyl (2-Isopropyl-5-Methyl Cyclohexyloxy) Dimethoxysilane (I-6)

Figure 5:
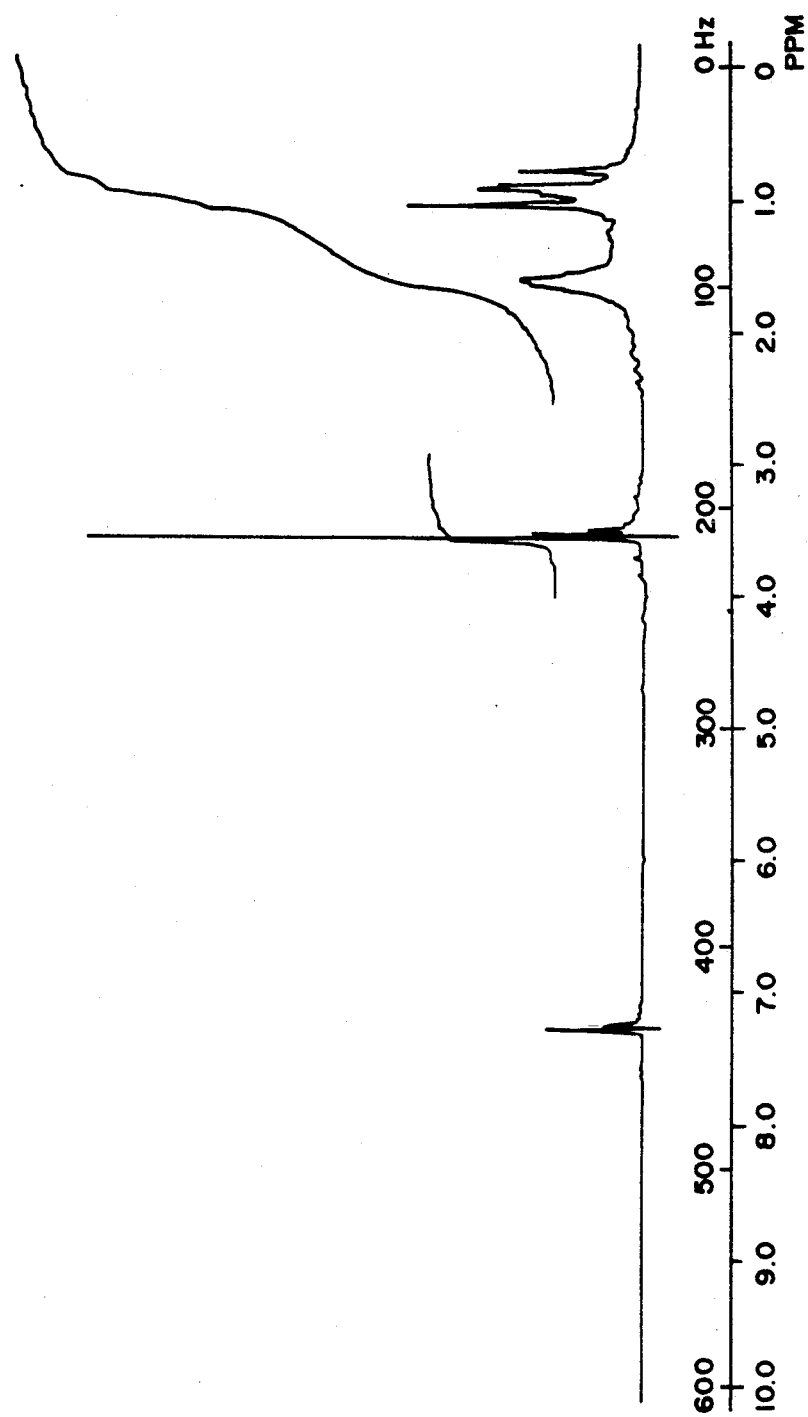
FIGS. 5 and 6 are charts of $^1$H-NMR and IR, respectively, on compound (I-6) obtained in Example 6.
Figure 6:
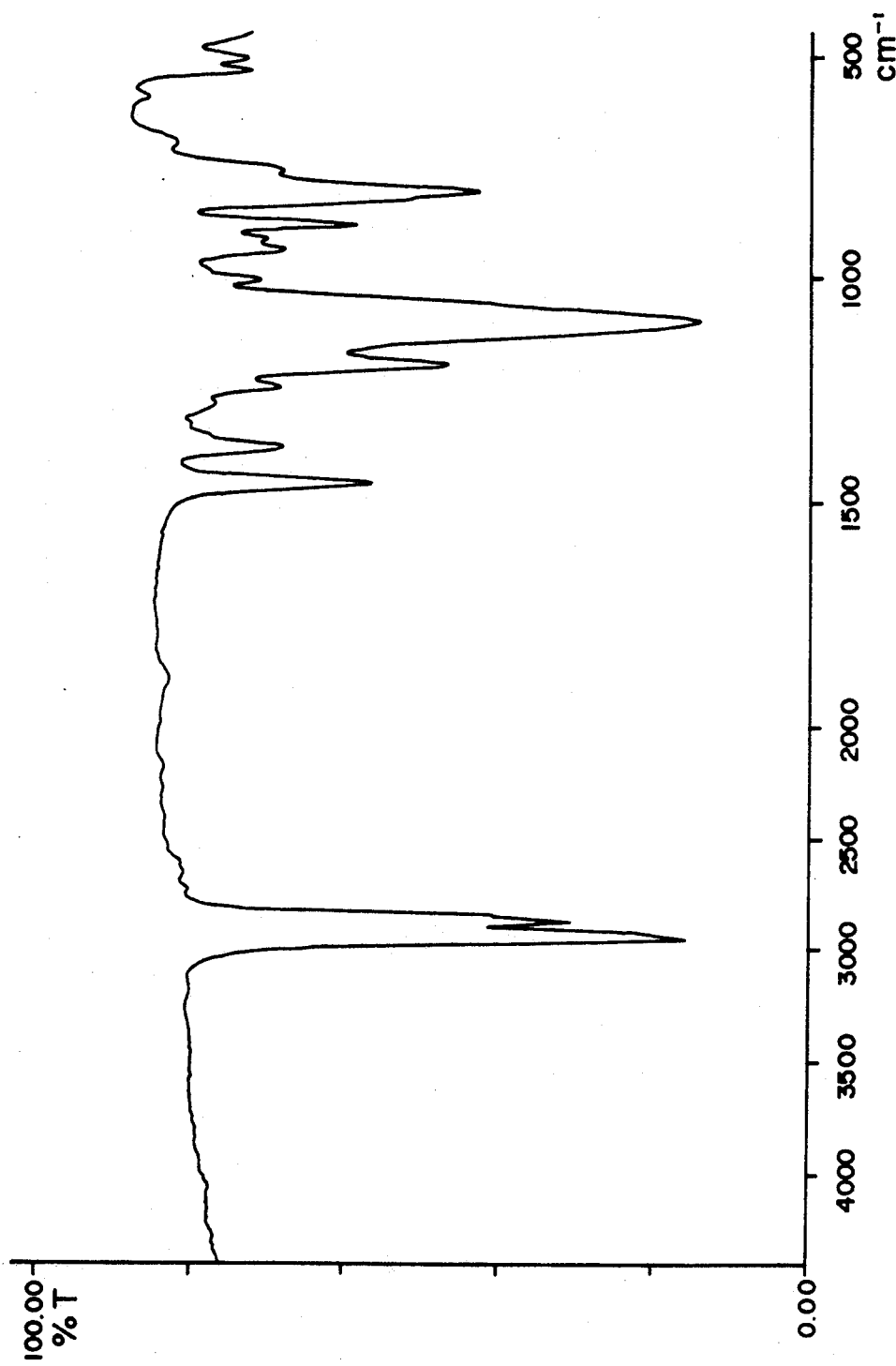

In a 100 ml three-neck flask provided with a magnetic stirrer and a reflux condenser were charged 10.8 g (0.0568 mole) of cyclopentyl trimethoxysilane, 44.4 g (0.284 mole) of (−)-menthol and 68.8 mg (1.27 m mole) of sodium methoxide, which were then heated under stirring in an oil bath of a temperature of 50° C. for 3 hours. After cooled, trimethylchlorosilane was added to neutralize the alkali. 16.3 g (0.0517 mole) of the product with a boiling point of 101° C./0.1 mmHg were obtained by vacuum distillation. This product was confirmed to be cyclopentyl (2-isopropyl-5-methyl cyclohexyloxy) dimethoxysilane as in Example 1. FIGS. 5 and 6 are the charts of $^1$H-NMR and IR, respectively. The yield was 91%.

EXAMPLE 7

Preparation of tert-Amyloxy Cyclopentyl Dimethoxysilane (I-2)

In a 100 ml autoclave were charged 13.5 g (0.198 mole) of cyclopentene, 24.4 g (0.180 mole) of trichlorosilane and 25 µl of a 0.077 m mole/ml chloroplatinic acid solution in isopropyl alcohol (platinum content $1.92 \times 10^{-6}$ mole), which were then stirred at 150° C. for 30 minutes. Cyclopentyl trichlorosilane was obtained quantitatively.

In a 500 ml three-neck flask provided with a magnetic stirrer, a reflux condenser and a dropping funnel were charged the cyclopentyl trichlorosilane prepared above and 300 ml of hexane, to which a mixture of 47.9 g (0.606 mole) of pyridine and 23.2 g (0.264 mole) of tert-amyl alcohol was added dropwise over a period of 30 minutes at room temperature under stirring.

After refluxing for further 2 hours, 17.9 g (0.558 mole) of methanol were added and refluxing was continued for further 1 hour and then the reaction was ended.

Figure 7:
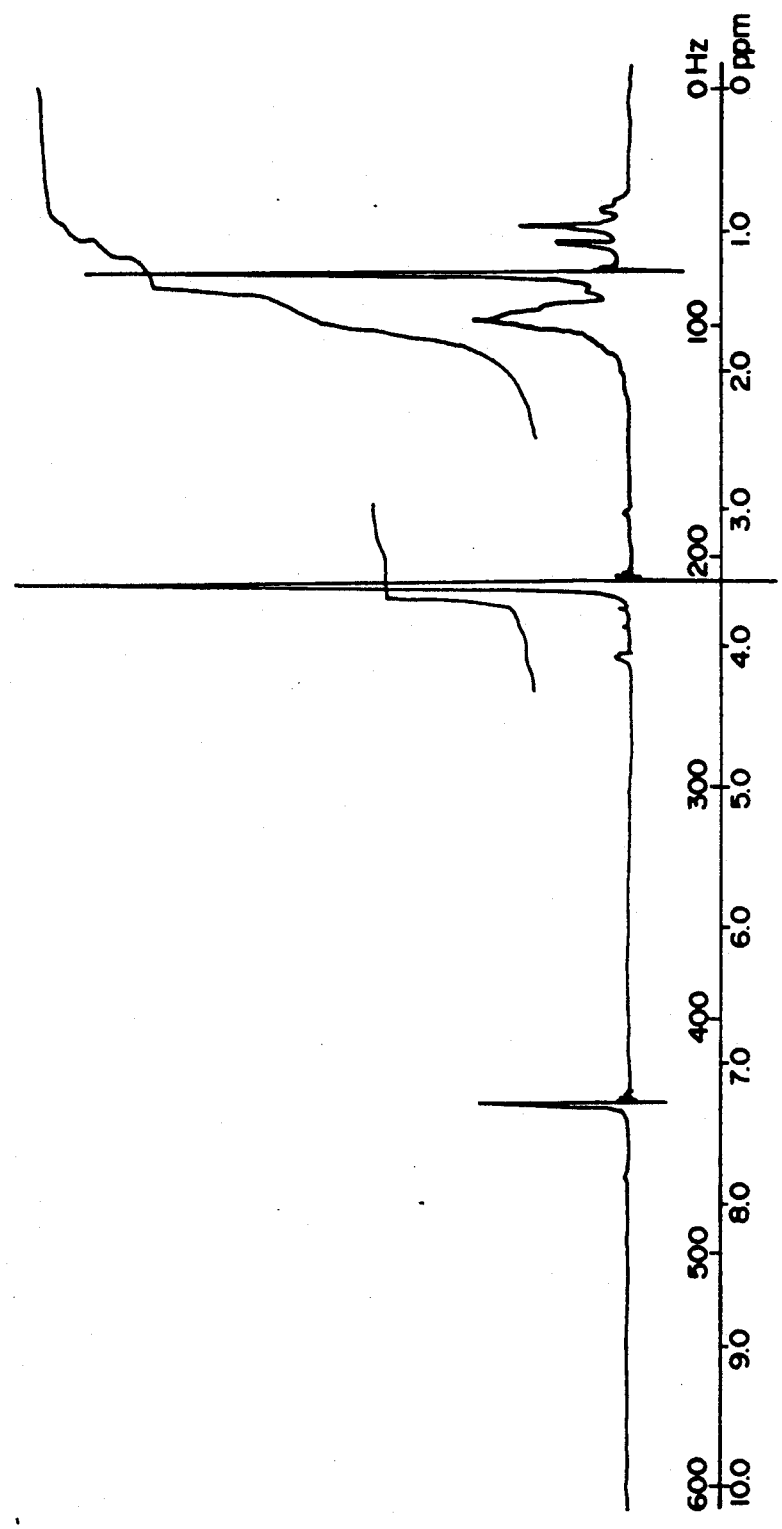
FIGS. 7 and 8 are charts of $^1$H-NMR and IR, respectively, on compound (I-2) obtained in example 7.
Figure 8:
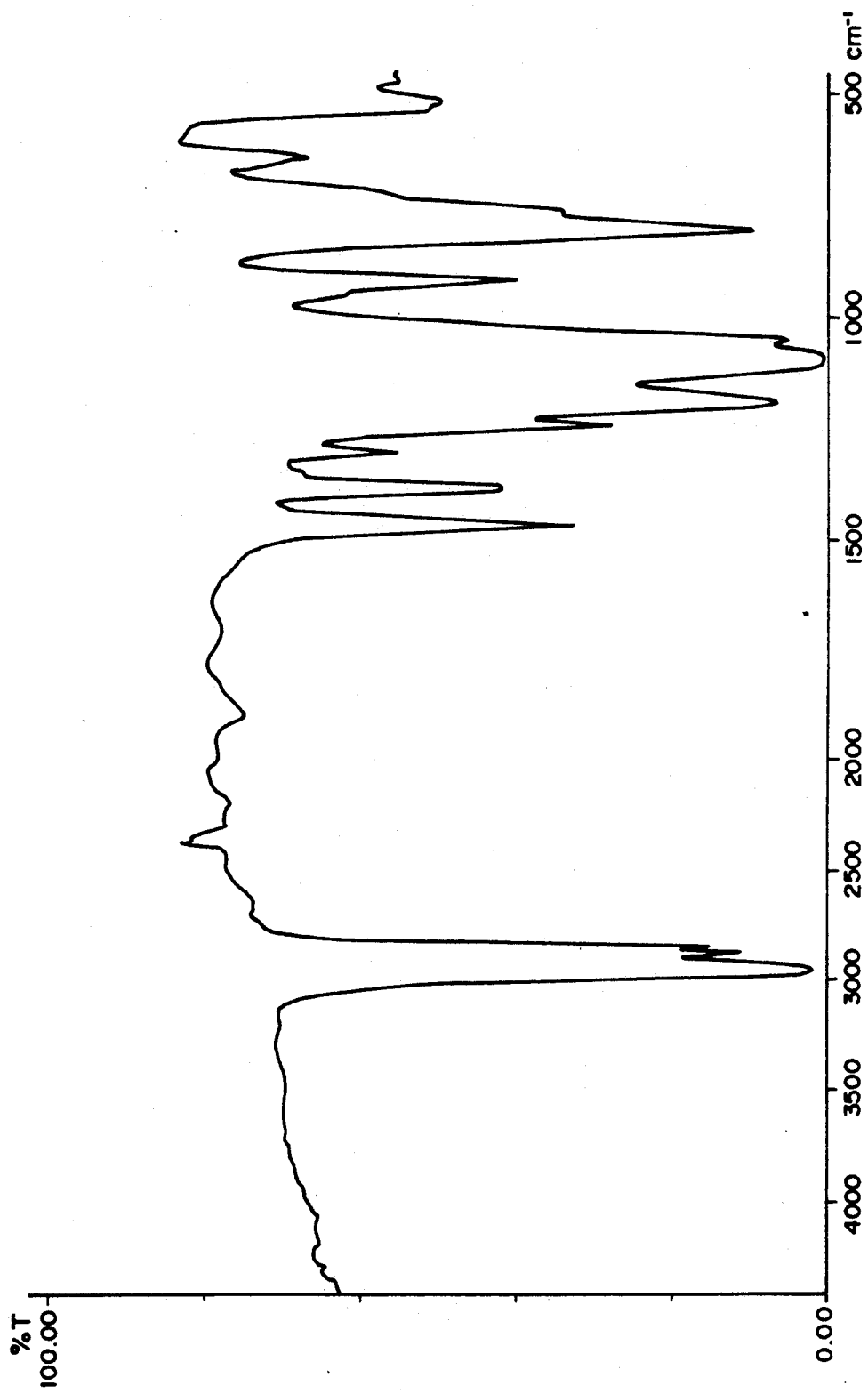

After a salt formed was filtered off and hexane was distilled off, a liquid of 34.8 g (0.141 mole) with a boiling point of 95° C./1.9 mmHg was obtained by vacuum distillation. This product was confirmed to be tert-amyloxy cyclopentyl dimethoxysilane by GC-MS, $^1$H-NMR and IR. The yield was 78%. FIGS. 7 and 8 are the charts of $^1$H-NMR and IR, respectively.

The GC-MS measurement results, m/e vs. spectral intensity ratios in parentheses, are as follows: 231(6), 217(19), 177(6), 159(16), 149(12), 131(16), 107(100), 91(22), 77(23), 59(16).

EXAMPLE 8

Another Preparation of tert-Amyloxy Cyclopentyl Dimethoxysilane (I-2)

In a 100 ml three-neck flask provided with a magnetic stirrer and a reflux condenser were charged 10.1 g (0.0531 mole) of cyclopentyl trimethoxysilane, 30.6 g (0.347 mole) of tert-amyl alcohol and 86.4 mg (1.6 m mole) of sodium methoxide, which were then reacted with each other in an oil bath of 105° C. for 4 hours under stirring. Then, trimethylchlorosilane was added to neutralize the alkali. Then, 10.7 g (0.0434 mole) of tert-amyloxy cyclopentyl dimethoxysilane were obtained by vacuum distillation. Its structure was confirmed as in Example 1. The yield was 82%.

EXAMPLE 9

Preparation of Cyclopentyloxy Cyclopentyl Dimethoxysilane (I-3)

In a 100 ml autoclave were charged 13.9 g (0.204 mole) of cyclopentene, 25.1 g (0.185 mole) of trichlorosilane and 25 µl of a 0.077 m mole/ml chloroplatinic acid solution in isopropyl alcohol (platinum content $1.92 \times 10^{-6}$ mole), which were then stirred at 150° C. for 30 minutes. Cyclopentyl trichlorosilane was obtained quantitatively.

In a 500 ml three-neck flask provided with a magnetic stirrer, a reflux condenser and a dropping funnel were charged the cyclopentyl trichlorosilane prepared above and 300 ml of hexane, to which a mixture of 49.3 g (0.623 mole) of pyridine and 19.1 g (0.222 mole) of cyclopentyl alcohol was added dropwise over a period of 30 minutes at room temperature under stirring.

After 2 hours reflux, 18.4 g (0.574 mole) of methanol were added and reflux was continued for further one hour and then the reaction was ended.

Figure 9:
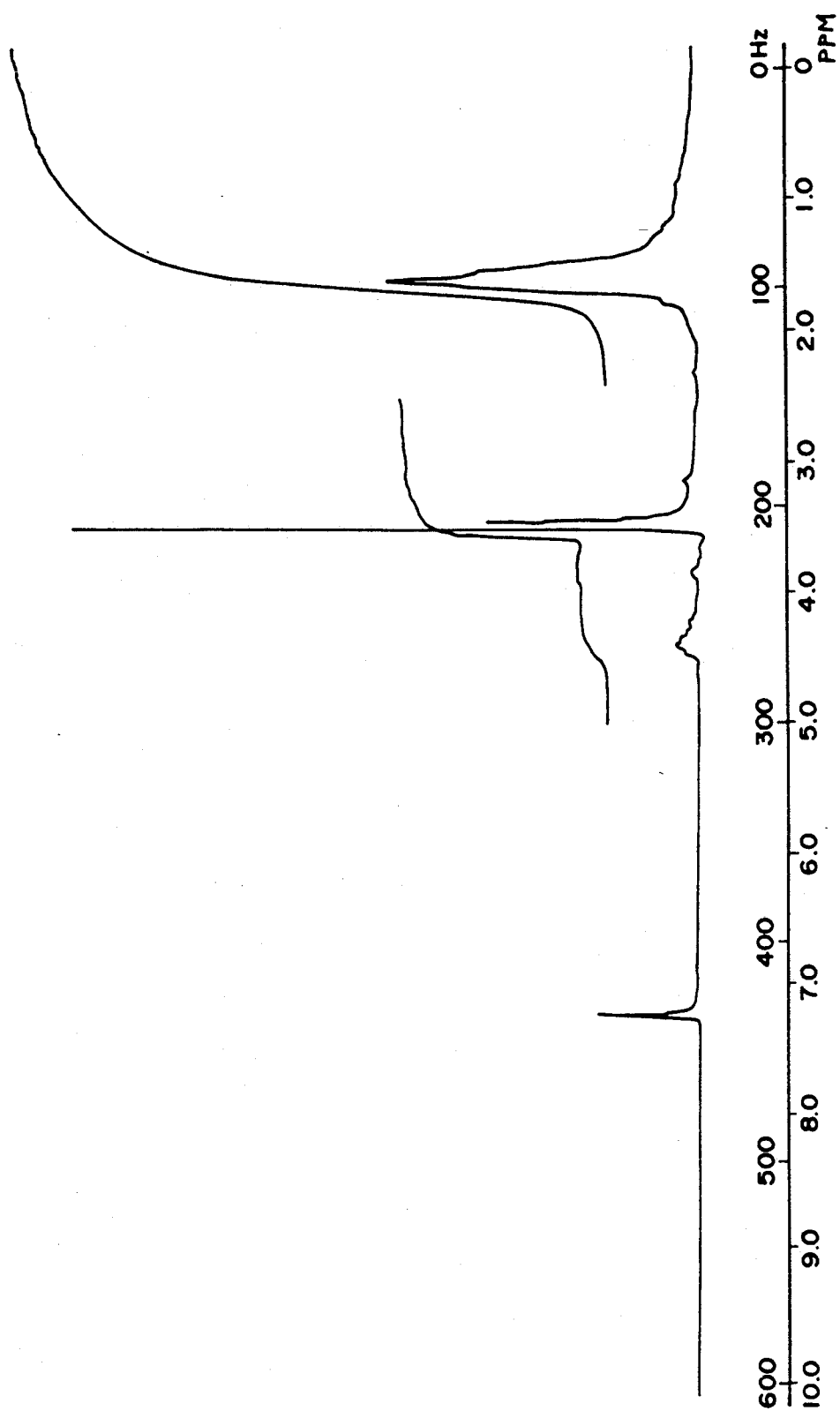
FIGS. 9 and 10 are charts of $^1$H-NMR and IR, respectively, on compound (I-3) obtained in Example 9.
Figure 10:
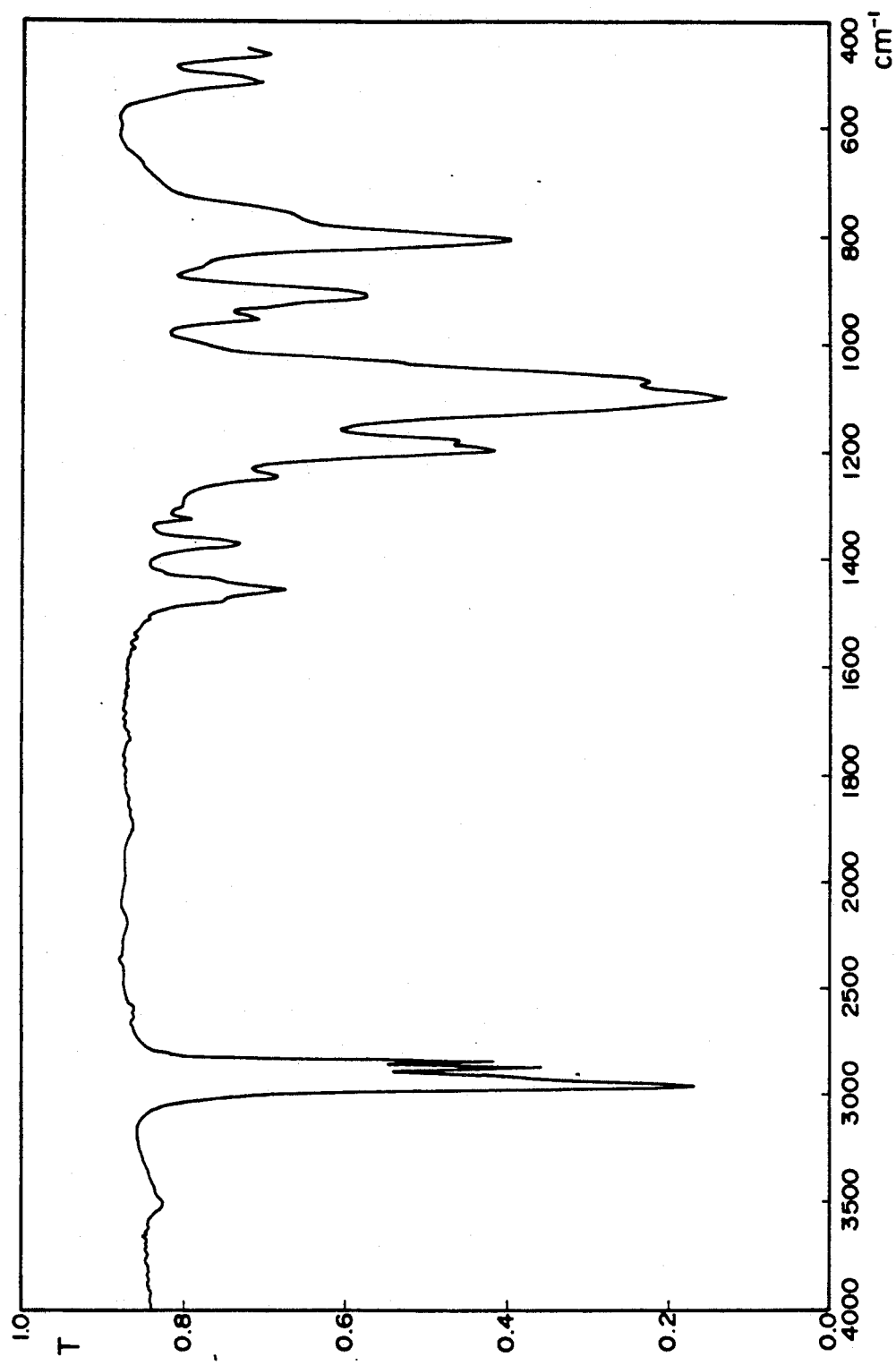

After a salt formed was filtered off and hexane was distilled off, a liquid of 31.0 g (0.127 mole) with a boiling point of 125° C./6 mmHg was obtained by vacuum distillation. This product was confirmed to be cyclopentyloxy cyclopentyl dimethoxysilane by GC-MS, $^1$H-NMR and IR. FIGS. 9 and 10 are the charts of $^1$H-NMR and IR, respectively. The yield was 69%.

The GC-MS measurement results, m/e vs. spectral intensity ratios in parentheses, are as follows: 177(7), 176(11), 175(67), 147(58), 131(11), 109(22), 107(100), 91(21), 77(23), 67(12).

EXAMPLE 10

Another Preparation of Cyclopentyloxy Cyclopentyl Dimethoxysilane (I-3)

In a 50 ml three-neck flask provided with a magnetic stirrer and a reflux condenser were charged 5.0 g (0.0262 mole) of cyclopentyl trimethoxysilane, 22.5 g (0.262 mole) of cyclopentyl alcohol and 18.6 mg (0.34 m mole) of sodium methoxide, which were then reacted with each other at room temperature for 2 hours under stirring. Then, trimethylchlorosilane was added to neutralize the alkali. Then, 5.4 g (0.0223 mole) of cyclopentyloxy cyclopentyl dimethoxysilane were obtained by vacuum distillation. Its structure was confirmed as in Example 1. The yield was 85%.

EXAMPLE 11

Preparation of Cyclopentyl Dimethoxy Oxa-3-Cyclopentyloxysilane (I-4)

In a 100 ml autoclave were charged 13.7 g (0.201 mole) of cyclopentene, 24.8 g (0.183 mole) of trichlorosilane and 25 μl of a 0.077 m mole/ml chloroplatinic acid solution in isopropyl alcohol (platinum content $1.92 \times 10^{-6}$ mole), which were then stirred at 150° C. for 30 minutes. Cyclopentyl trichlorosilane was obtained quantitatively.

In a 500 ml three-neck flask provided with a magnetic stirrer, a reflux condenser and a dropping funnel were charged the cyclopentyl trichlorosilane prepared above and 300 ml of hexane, to which a mixture of 53.6 g (0.678 mole) of pyridine and 25.8 g (0.293 mole) of 3-hydroxy tetrahydrofurane was added dropwise over a period of 30 minutes at room temperature under stirring.

After 2 hours reflux, 19.0 g (0.593 mole) of methanol were added and reflux was continued for further one hour and then the reaction was ended.

Figure 11:
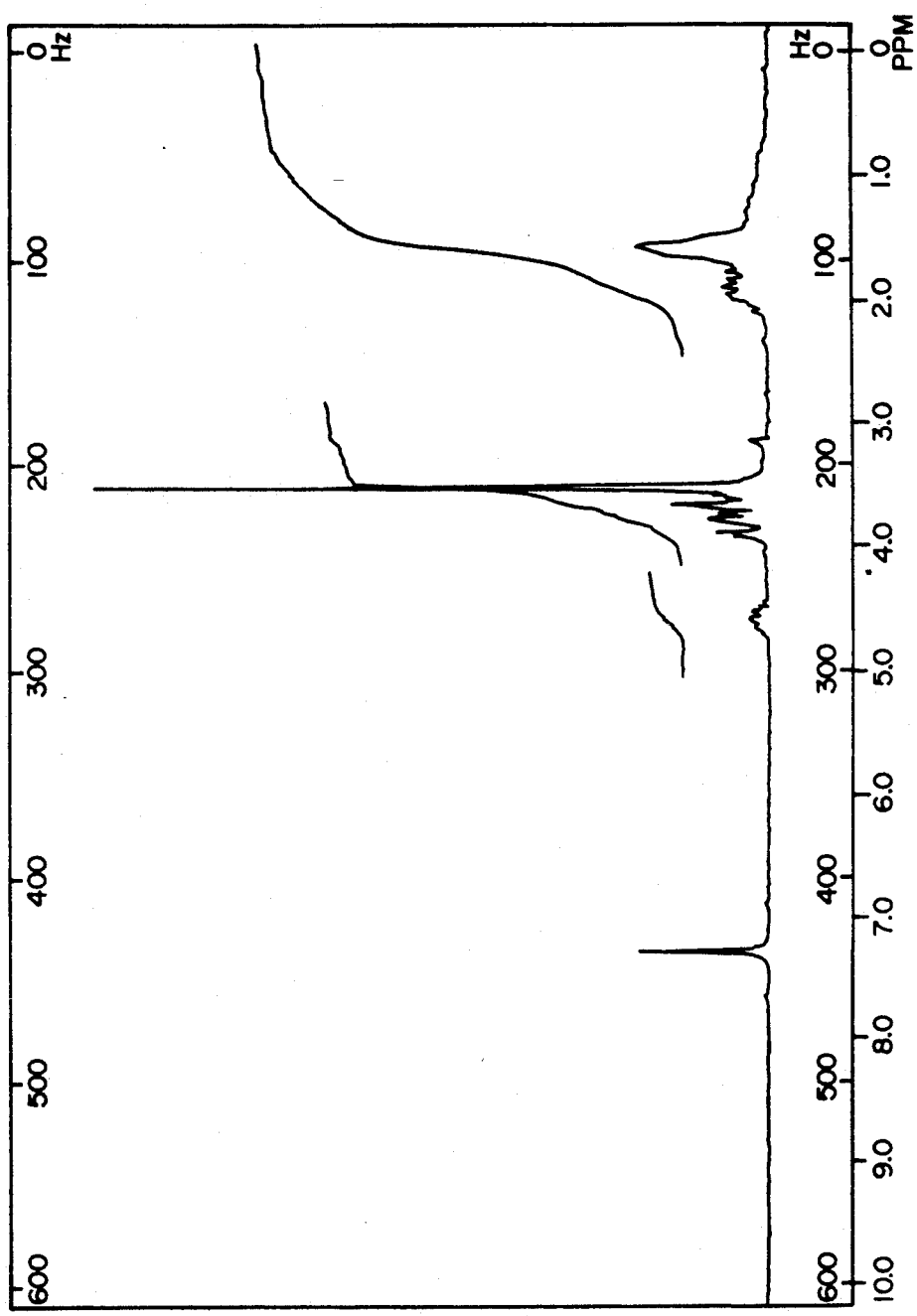
FIGS. 11 and 12 are charts of $^1$H-NMR and IR, respectively, on compound (I-4) obtained in Example 11.
Figure 12:
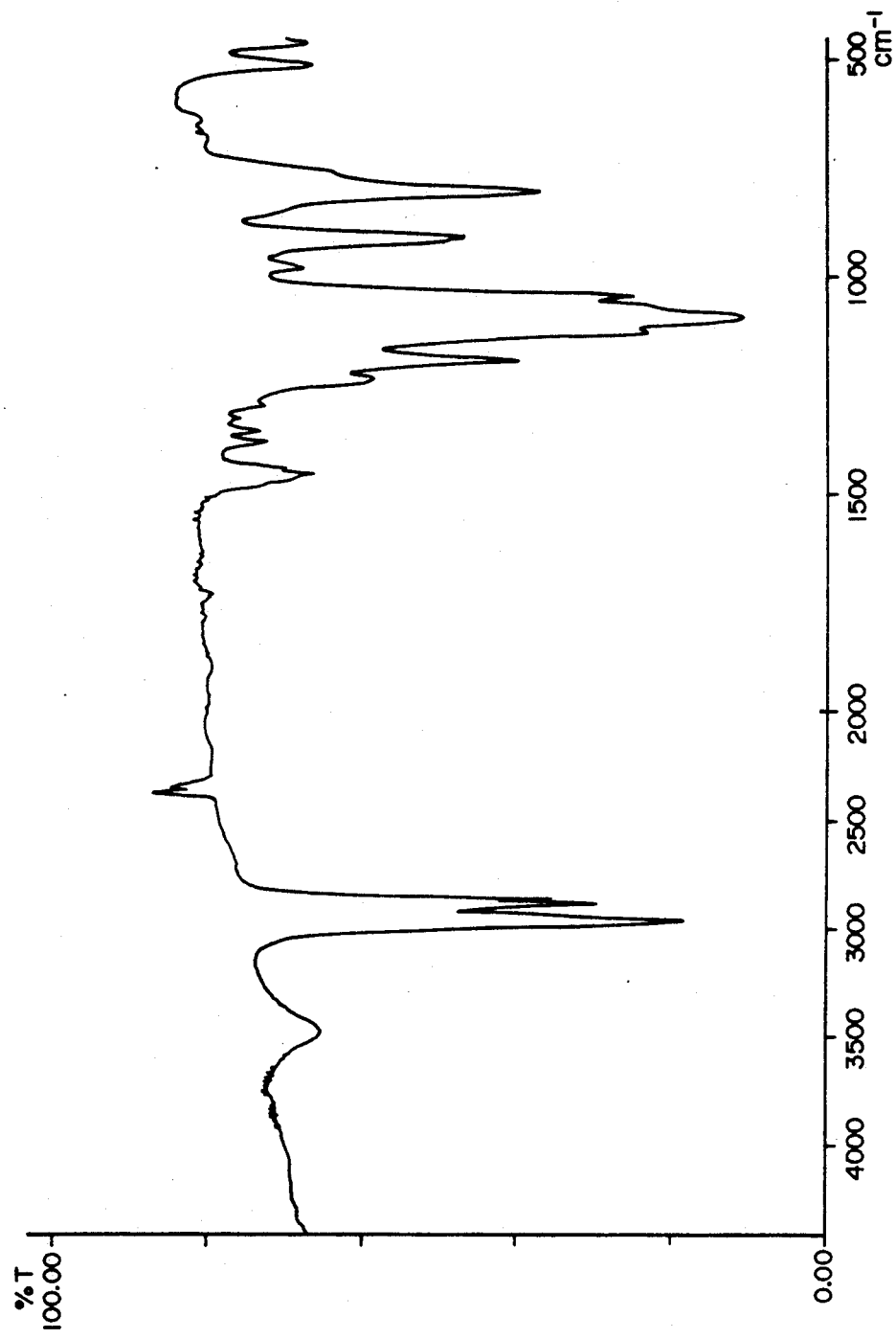

After a salt formed was filtered off and hexane was distilled off, a liquid of 22.8 g (0.0925 mole) with a boiling point of 77° C./10 mmHg was obtained by vacuum distillation. This product was confirmed to be cyclopentyl dimethoxy oxa-3-cyclopentyloxysilane by GC-MS, $^1$H-NMR and IR. FIGS. 11 and 12 are the charts of $^1$H-NMR and IR, respectively. The yield was 46%.

The GC-MS measurement results, m/e vs. spectral intensity ratios in parentheses, are as follows: 177(11), 150(10), 149(100), 119(13), 91(22), 77(11), 41(10).

EXAMPLE 12

Another Preparation of Cyclopentyl Dimethoxy Oxa-3-Cyclopentyloxysilane (I-4)

In a 100 ml three-neck flask provided with a magnetic stirrer and a reflux condenser were charged 7.7 g (0.0404 mole) of cyclopentyl trimethoxysilane, 35.7 g (0.405 mole) of 3-hydroxy tetrahydrofurane and 53.0 mg (0.98 m mole) of sodium methoxide, which were then reacted with each other in an oil bath of 80° C. for 2 hours under stirring. After cooled, trimethylchlorosilane was added to neutralize the alkali. Then, 5.37 g (0.0218 mole) of cyclopentyl dimethoxy oxa-3-cyclopentyloxysilane were obtained by vacuum distillation. Its structure was confirmed as in Example 1. The yield was 54%.

What we claim is:

1. A silane compound represented by the following formula (I):

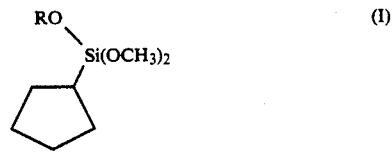

wherein R represents an organic group selected from the group consisting of sec-butyl, tert-amyl, cyclopentyl, oxa-3-cyclopentyl, cyclohexyl and 2-isopropyl-5-methyl cyclohexyl groups.

* * * * *